United States Patent [19]
Monson

[11] Patent Number: 5,355,815
[45] Date of Patent: Oct. 18, 1994

[54] CLOSED-LOOP VARIABLE RATE APPLICATOR

[75] Inventor: Robert J. Monson, St. Paul, Minn.

[73] Assignee: Ag-Chem Equipment Co., Inc., Minnetonka, Minn.

[21] Appl. No.: 33,911

[22] Filed: Mar. 19, 1993

[51] Int. Cl.$^5$ ............................................. A01C 15/00
[52] U.S. Cl. .................................. 111/200; 111/903; 111/127; 356/301
[58] Field of Search ............... 111/200, 130, 903, 127; 239/63, 67, 69; 356/446, 72, 301

[56] References Cited

U.S. PATENT DOCUMENTS

| | | | |
|---|---|---|---|
| 3,881,353 | 5/1975 | Fathauer | 111/903 |
| 4,246,469 | 1/1981 | Merlo | 111/903 |
| 4,266,878 | 5/1981 | Auer . | |
| 4,545,396 | 10/1985 | Miller et al. | 239/69 |
| 4,776,690 | 10/1988 | Quimby | 356/72 |
| 4,799,799 | 1/1989 | Sapko et al. | 356/446 |
| 4,969,741 | 11/1990 | Kennedy et al. | 356/301 |
| 4,979,123 | 12/1990 | Yang | 356/301 |
| 5,033,397 | 7/1991 | Colburn, Jr. | 111/300 |
| 5,044,756 | 9/1991 | Gaultney et al. . | |
| 5,090,806 | 2/1992 | Pierce | 356/301 |
| 5,143,224 | 9/1992 | Burchell | 356/301 |
| 5,220,876 | 6/1993 | Monson et al. | 111/130 |
| 5,255,067 | 10/1993 | Carrabba et al. | 356/301 |

FOREIGN PATENT DOCUMENTS

8912510  12/1989  World Int. Prop. O. ............ 239/63

OTHER PUBLICATIONS

"Instant Raman . . . " brochure by Chromex Raman One.
"Parallel Spectroscopy" brochure by Chromex II.
"Chromex-Technical Note 5" brochure dated Oct. 1991.
"Photo Research"-PR-704/PR-714-Spectrascan Systems brochure.
"Chromex-250IS & 500IS-Imaging Spectrographs" brochure by Chromex II.

Primary Examiner—Randolph A. Reese
Assistant Examiner—Spencer Warnick
Attorney, Agent, or Firm—Haugen & Nikolai

[57] ABSTRACT

A closed-loop fertilizer application system capable of determining a soil prescription in near real-time, and dispensing fertilizer to the soil scene as a function of the soil prescription. The closed loop application system does not require the use of maps or navigation systems, but rather, ascertains a soil type and chemical composition on the go. In the preferred embodiment, the application system implements a spectrograph implementing the technology of spectroradiometry to determine soil type and present fertilizer composition in near real-time. An expert system determines the soil prescription based on the soil type and current fertilizer levels, and controls the dispensing rate of the fertilizer as a function of the vehicle speed. The soil analyzer is disposed a predetermined distance forward of the vehicle such that there is adequate time to perform soil analysis, determine a soil prescription, and then dispense the fertilizer at the rear portion of the vehicle. The soil analyzer generates a soil signature in near real time, which signature is compared to a pre-determined reference soil signature stored in memory. The spectrograph radiates the soil at various pre-determined fixed frequencies which causes the various elements in the soil to fluoresce. Each fertilizer in the soil will fluoresce at one or more known frequencies, the amplitude of which is indicative of the percentage of the fertilizer present at the soil scene.

20 Claims, 5 Drawing Sheets

CLOSED-LOOP VARIABLE RATE APPLICATOR

CROSS REFERENCE TO RELATED APPLICATION

Cross reference is made to co-pending application entitled Variable Rate Application System assigned Ser. No. 07/902,174 and filed Jun. 22, 1992 now U.S. Pat. No. 5,220,876.

FIELD OF THE INVENTION

The present invention relates generally to an application system for applying fertilizer to agricultural land, and more particularly to a method and apparatus for ascertaining a current fertilizer content of a soil scene in near real-time, and then determining a chemical prescription and dispensing fertilizer on the land without the need for a navigation system or digital fertilizer maps.

BACKGROUND OF THE INVENTION

In the fertilizer industry, there is a growing awareness of environmental concerns and the ability of a custom applicator to answer those concerns. As discussed in the co-pending related application identified above, a variable rate technology can be implemented using a plurality of maps containing soil-type information, current fertilizer levels and desired fertilizer levels, used in combination with a navigation system to create a chemical prescription.

As is well known, the three most common nutrient components of soil are nitrogen, phosphorous and potassium. Differing soil types, each of which may be categorized according to the relative proportions of sand, clay and silt, have differing percentages of these nutrients. Even like soil types can have differing percentages of these nutrients within agricultural land due to drainage characteristics, moisture content and erosion. Thus, fertilizer application systems need to account for the present levels of fertilizers at each location of the agricultural field to determine a chemical prescription when applying fertilizers to achieve desired fertilizer levels. One embodiment of the fertilizer application system discussed in the above-referenced co-pending application includes a plurality of maps storing soil types, and present and desired fertilizer levels within a field. Using a navigation system and a speed sensor, the system coordinates the vehicles location within the field to each of the maps to determine the application rate of fertilizers to attain the desired levels of fertilizers.

While navigation systems currently available are becoming increasingly more accurate in resolution, such as Global Positioning Systems, there still can be an alignment difficulty based on the inherent inaccuracies of the source data utilized to create the map. Thus, a closed-loop application system which would eliminate the coordination of the navigation positioning system to the soil and fertilizer maps, and would be an advancement over prior art systems. Up until now, soil analyzers capable of sampling soil for chemical content in near real-time were unavailable, thus requiring soil maps and fertilizer maps to be first created by a soil scientist, and then digitized for subsequent use by the application equipment. Due to various uncertainties in the analysis, these maps may differ from the real world conditions at time of fertilizer application due to time, weather, miscalculations, or a variety of other problems.

U.S. Pat. No. 5,044,756 to Gaultney et al. teaches a real-time soil organic matter sensor. This sensor is adapted to a vehicle to determine organic matter content of soil at a soil scene. This device uses a light source which generates light at a fixed frequency, and senses the intensity of the reflected light at the same fixed frequency to determine the organic matter content. This device is limited to obtaining only organic matter content of soil based upon a percentage of the reflected light of a fixed frequency, and does not form a portion of an fertilizer application system.

OBJECTS

It is accordingly a principle object of the present invention to provide a closed-loop fertilizer application system which does not require the use of a navigation positioning system.

It is a further object of the present invention to provide a closed-loop fertilizer application system which does not require maps of current fertilizer levels.

Still yet another object of the present invention is to provide a closed-loop fertilizer application system including a soil analyzer capable of analyzing soil for chemical content in real-time and with high accuracy.

Other objects, features and advantages of the present invention will become apparent to those skilled in the art through the Description of the Preferred Embodiment, Claims, and drawings herein, wherein like numerals in the various figures relate to like elements.

SUMMARY OF THE INVENTION

The foregoing features and advantages of the present invention are achieved by providing a closed-loop fertilizer application system which determines a chemical prescription in real-time for a soil scene, depending on the soil fertilizer content ascertained by a soil analyzer in real-time, and which dispenses fertilizer on the soil scene in response to the chemical prescription. Preferably, the soil analyzer comprises a spectrograph performing spectroradiometric measurements to provide a non-contact method of ascertaining soil chemistry. The fertilizer application system comprises a vehicle capable of traversing a field. A soil analyzer capable of obtaining a soil signature indicative of the fertilizer content of a soil scene is adapted to the vehicle. The soil analyzer comprises a signal generator generating a first signal at a fixed frequency and directed towards the soil scene. The soil analyzer also comprises a detector for detecting a returned second signal from the soil scene induced by the first signal. The second signal is composed of a plurality of frequencies and defines the soil signature. A dispenser apparatus is connected to the vehicle and is responsive to the soil analyzer for dispensing at least one type of product at a rate dependent upon the detected soil signature.

Preferably, the soil analyzer comprises a spectrograph radiating the soil scene at a pre-determined fixed frequency, wherein a spectrum of returned second signals is detected by the soil analyzer. The dispenser apparatus compares the detected soil signature to a pre-determined soil signature stored therein and determines a soil prescription dependent upon the differences between the detected and pre-determined soil signatures, and then dispenses the product at a rate dependent upon the soil prescription and the vehicle speed. Using a spectrograph, the spectrograph determines the intensity of the returned spectrum of second signals. The dispenser apparatus compares the intensity of the detected second signals to the intensity of the pre-determined soil signature, preferably at one or more pre-determined frequencies where spikes occur. Ideally, the pre-determined soil signature represents the soil signature a soil scene comprised of 100 percent of a particular product. Thus, the ratio of the determined intensity to the pre-determined intensity at a spike at a common wavelength is indicative of the percentage of the product sensed at the soil scene.

A further feature of the present invention is that the soil analyzer can perform real-time averaging of the intensities of the detected second signals. The dispenser apparatus then dispenses the product as a function of the averaged second signals. Since the second signals are averaged over time, a more uniform distribution of fertilizers is obtained. In the preferred embodiment, the soil signature is indicative of the nitrogen, phosphorous and potassium chemicals at the soil scene.

The soil analyzer is preferably coupled to the vehicle at predetermined forward location of the vehicle, wherein the dispenser is positioned at a pre-determined distance behind the soil analyzer. Thus, as the vehicle traverses the field at a fixed speed, there will be an inherent time delay between when the soil analyzer passes over and analyzes a particular soil scene and when the dispenser passes thereover. This inherent time delay is adequate for the soil analyzer to obtain a soil signature, and for the dispenser apparatus which includes an expert system to process the soil signature obtained from the soil analyzer and subsequently dispense the appropriate amount of chemicals on the soil scene. Using a spectrograph, the soil analysis can be performed in a matter of milliseconds. Thus, the time delay for the dispenser apparatus to process the soil signature and dispense the chemicals primarily determines how far forward of the dispenser the soil analyzer needs to be disposed if the vehicle is to traverse the field at a particular speed.

DESCRIPTION OF THE PREFERRED EMBODIMENT

Figure 1:
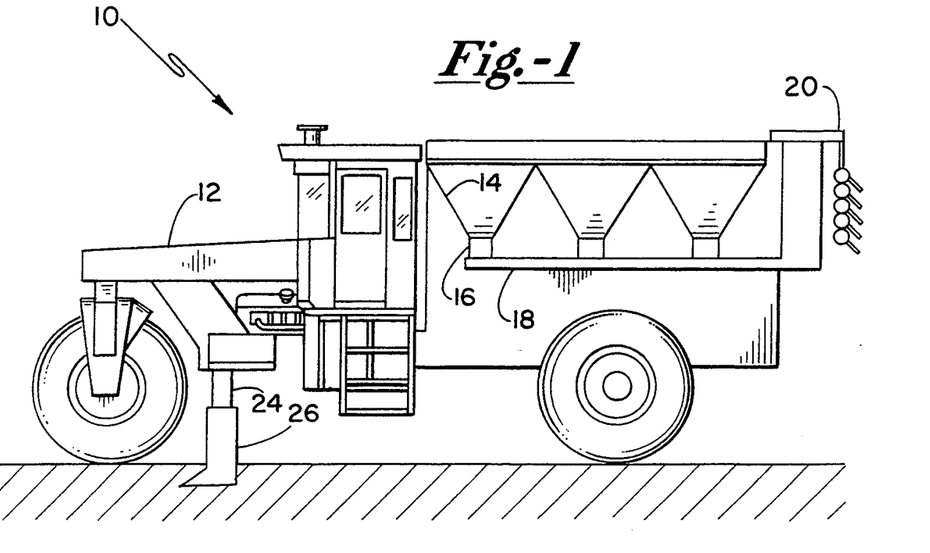
FIG. 1 is a side elevational view of a dispensing vehicle having a soil analyzer at a forward location of the vehicle, and with a dispensing assembly at a rearward location thereof.
Figure 2:
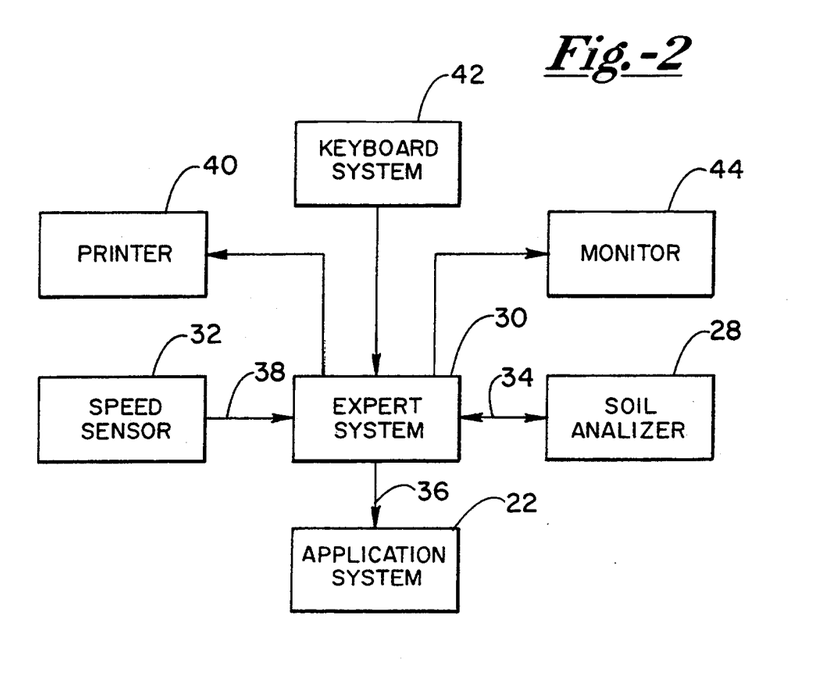
FIG. 2 is a block diagram of the soil application system controlled by an expert system, which expert system controls the application system as a function of the speed sensor and the soil signature from the soil analyzer.

Referring to FIG. 1, a side elevational view of a closed-loop fertilizer application system according to the present invention is generally shown at 10. System 10 comprises a vehicle 12, such as a tractor, capable of traversing an agricultural field. Tractor 12 includes a plurality of product bins 14 for storing a plurality of fertilizer blends, such as nitrogen, phosphorous and potassium. Fertilizer is dispensed from each respective bin 14 by a respective dispenser 16 to conveyor 18 at a rate controlled by expert system 30. (See FIG. 2). The dispensed fertilizers are conveyed by conveyor 18 to a pneumatic spreader or dispenser apparatus 20, as taught by U.S. Pat. No. 5,028,009 assigned to the present applicant and incorporated herein by reference. Product bin 14, dispenser 16, conveyor 18 and spreader 20 form an application system 22 which is controlled by expert system 30 as shown in FIG. 2. The apparatus described so far is well-known in the art and discussed in the cross referenced co-pending application, the teachings of which are incorporated herein by reference.

Still referring to FIG. 1, system 10 further includes a vertically oriented elongated support structure 24 which is secured to a forward portion of the frame of vehicle 12 and is disposed a pre-determined distance forward of dispenser 20. The lower end of structure 24 extends downward towards the soil and is telescopingly coupled to a soil cutting knife 26, which knife is well-known in the art. Cutting knife 26 extends a selectable pre-determined distance into the soil due to the telescoping feature and generates a furrow as vehicle 12 traverses the field. Knife 26 generates a furrow with a flat bottom as it is traversed through the field, the flat bottom furrow forming the soil scene. A soil analyzer 28 is securingly disposed within knife 26, and is disposed proximate the soil scene (flat portion of the furrow), but is spaced a predetermined distance thereabove to define a non-contact sensor. Thus, soil analyzer 28 will not become damaged or obstructed by soil as knife 26 is traversed through the soil. A speed sensor 32 (see FIG. 2) is provided within vehicle 12 for providing an output indicative of the speed of vehicle 12 relative to the soil.

Now referring to FIG. 2, a block diagram of the closed-loop fertilizer application system according to the preferred embodiment of the invention is shown. As discussed earlier, soil analyzer 28 is operatively coupled to expert system 30 via line 34. Expert system 30 is a multitasking processing system based, for example, on a UNIX operating system. Expert system 30 is the heart of the system for it coordinates and operates in response to other major subsystems to control the dispensing rate of multiple fertilizer blends contained in the respective bins 14. Expert system 30 resides within the cab of vehicle 12 and controls application system 22 via line 36. Expert system 30 and application system 22 define a dispensing mechanism. A speed sensor 32, such as a radar based sensor, is coupled to expert system 30 via line 38 for providing expert system 30 with vehicle speed.

Soil analyzer 28 preferably comprises a spectrograph, such as model PR-704/PR-714 manufactured by the Photo Research Company of Chatsworth, Calif. A key feature of soil analyzer 28 is its ability to analyze the soil scene for chemical composition in near real-time, and provide a spectra forming a soil signature, typically in as little as 26 milliseconds. Soil analyzer 28 is PC-compatible, and expert system 30 can respond to the output from soil analyzer 28 in near real-time. Expert system 30 determines a soil prescription based on the spectra, and then instructs control application system 22 to dispense a blend of fertilizers at a rate depending upon the determined soil chemical composition, and vehicle speed. Expert system 30 can process the output from soil analyzer 28 in approximately 100 milliseconds to determine a chemical prescription for the soil scene, and spreader 20 can react to the instructions from expert system 30 in approximately 0.5 seconds. Thus, when vehicle 12 travels at 18 miles an hours the vehicle would travel approximately 9½ inches while soil analyzer 28 is completing its measurement, 31.7 inches while expert system 30 is determining the chemical prescription based on the spectra from the soil analyzer 28, which is the soil signature, and approximately 13 feet while spreader 20 is reacting to the commands from expert system 30. Thus, support structure 24 (see FIG. 1), and knife 26 and soil analyzer 28 defined therein is positioned at least 16 feet, and preferably 20 feet, forward of dispenser 20 for a vehicle traveling at 18 miles an hour.

By reducing the response time of spreader 20, the minimum required separation of sensor 28 and spreader 20 can be reduced for a given vehicle speed. For instance, by reducing the reaction time of spreader 20 to 0.25 seconds, a net separation between soil analyzer 28 and spreader 20 of 10 feet is required for a vehicle traveling at 18 miles an hour.

A key feature of soil analyzer 28 used with expert system 30 is the ability to accurately determine the presence and percent of specific fertilizers within at the soil scene, as well as the ability to determine the type of soil, in near real-time. The spectrograph performs soil analysis operating on the principle of spectroradiation, which is radiating the soil with an illumination source at a selected fixed frequency to cause the elements of interest to fluoresce or glow. A spectral radiance of each of the chemicals of interest is measured by the spectrograph, wherein the spectrograph produces a spectrographic image of the soil scene measured. Different elements, such as nitrogen, potassium, phosphorous and zinc are excited by a selected fixed, but different, frequency illumination source. Nitrogen, potassium, phosphorous and zinc will each fluoresce optimally when excited by a source (laser) of differing frequencies. For instance, potassium will optimally fluoresce when excited by a 766.4 nm. wavelength source, nitrogen at 1246.9 nm., phosphorous at 956.3 nm., and zinc at 636.2 nm. The various wave lengths at which each of the elements radiates or peaks is unique, and the intensities of the peaks are dependent upon the wave length of the illumination source. Due to quantum mechanics, each element will produce a spectral image unique to the next for a given illumination source, allowing the spectral images to be distinguished.

Figure 3:
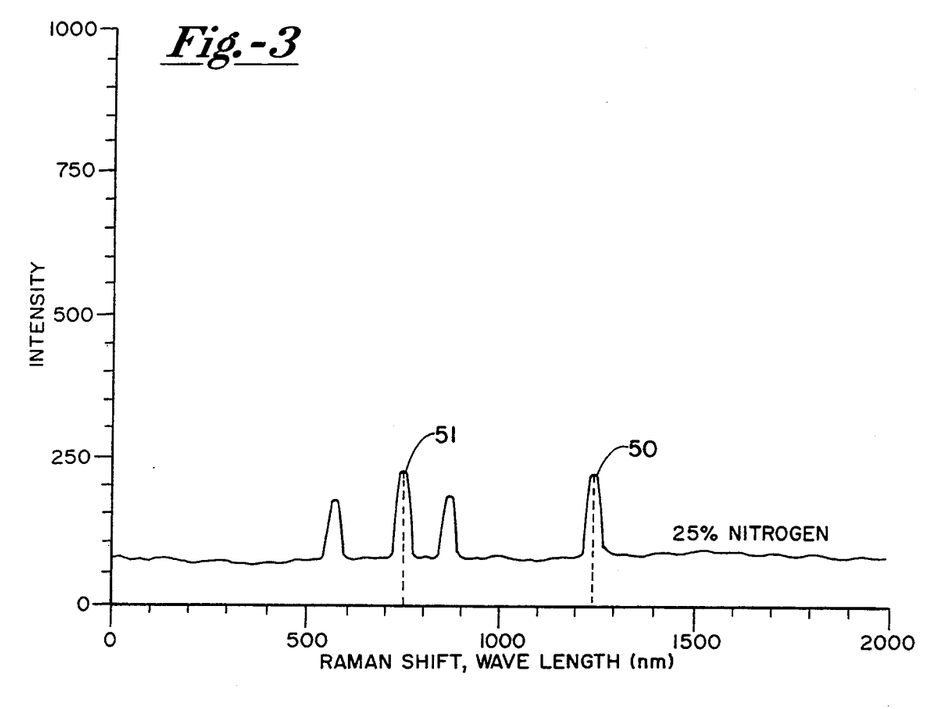
FIGS. 3, 4 and 5 are graphs of several spectra sensed by the spectrograph at a soil scene. The Raman shift is illustrated as a function of intensity for each of three chemicals under-study, wherein each of the three spectra are scaled to one another, and are obtained using a different source frequency chosen on the basis of which chemical is to be studied.
Figure 4:
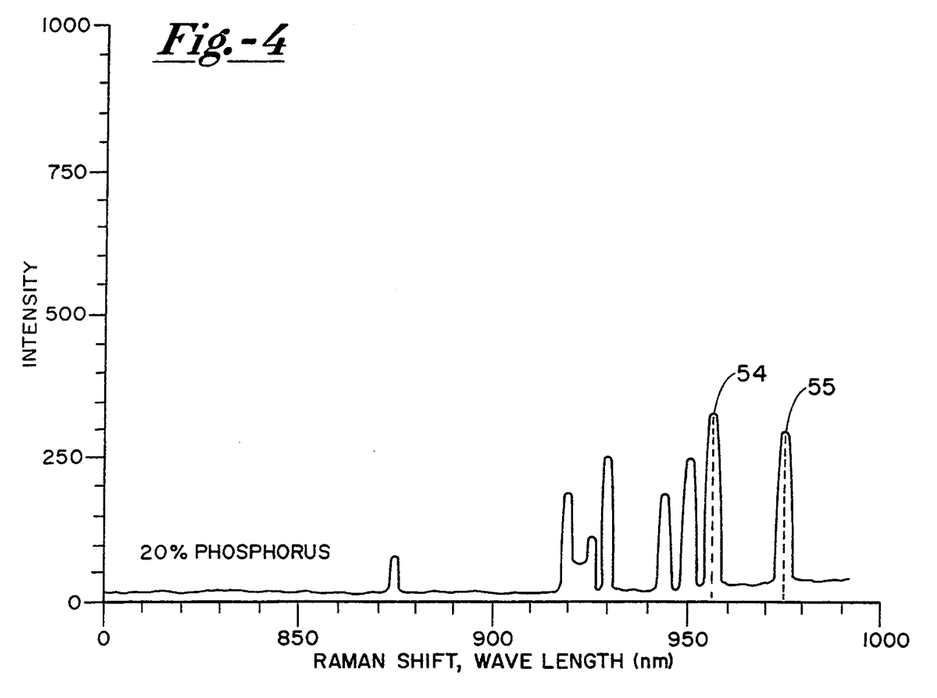
Figure 5:
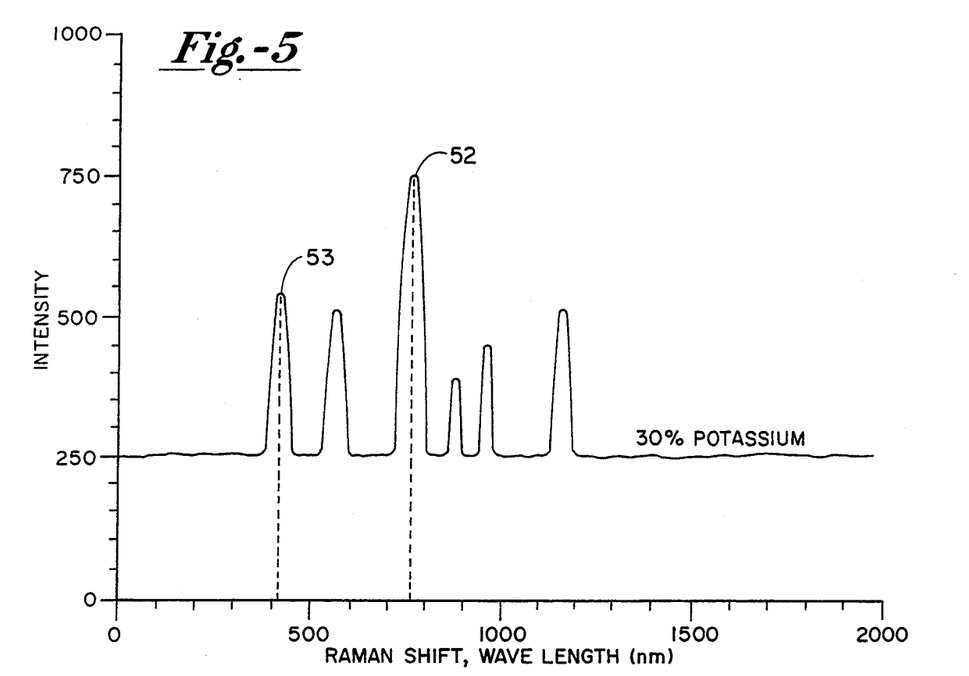
Figure 6:
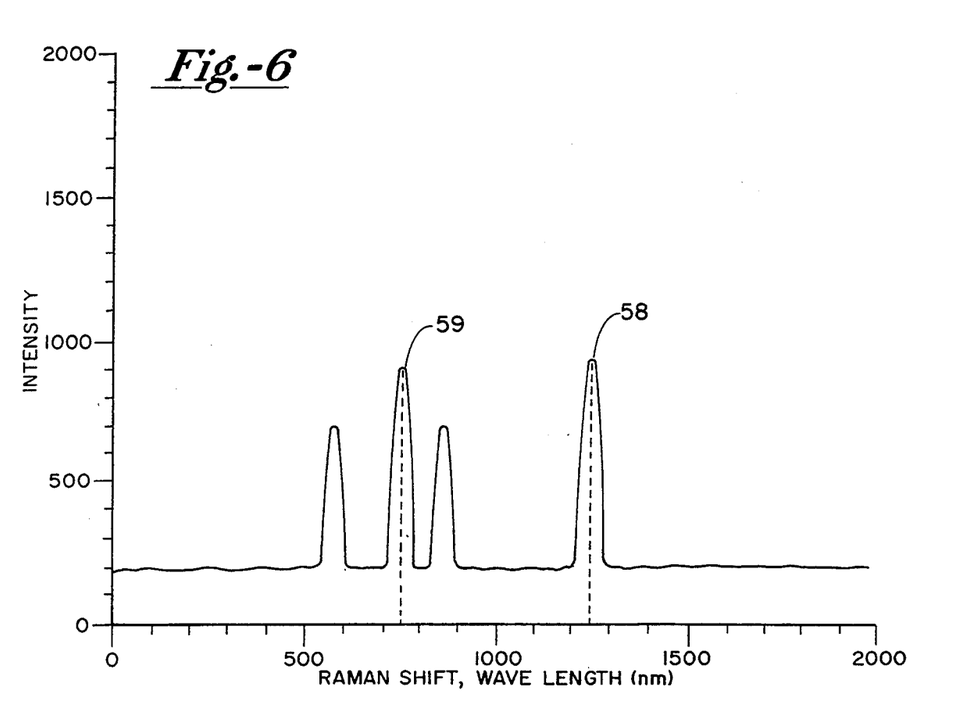
FIGS. 6, 7 and 8 illustrate a reference spectrograph obtained from separate soil scene comprised entirely of nitrogen, phosphorus and potassium, respectively. The respective obtained spectra in FIGS. 3, 4 and 5 are compared against the respective spectra of FIGS. 6, 7 and 8 wherein the ratio of intensities at one or more peak frequencies between the respective Figures is indicative of the percentage of that chemical in the soil scene.
Figure 7:
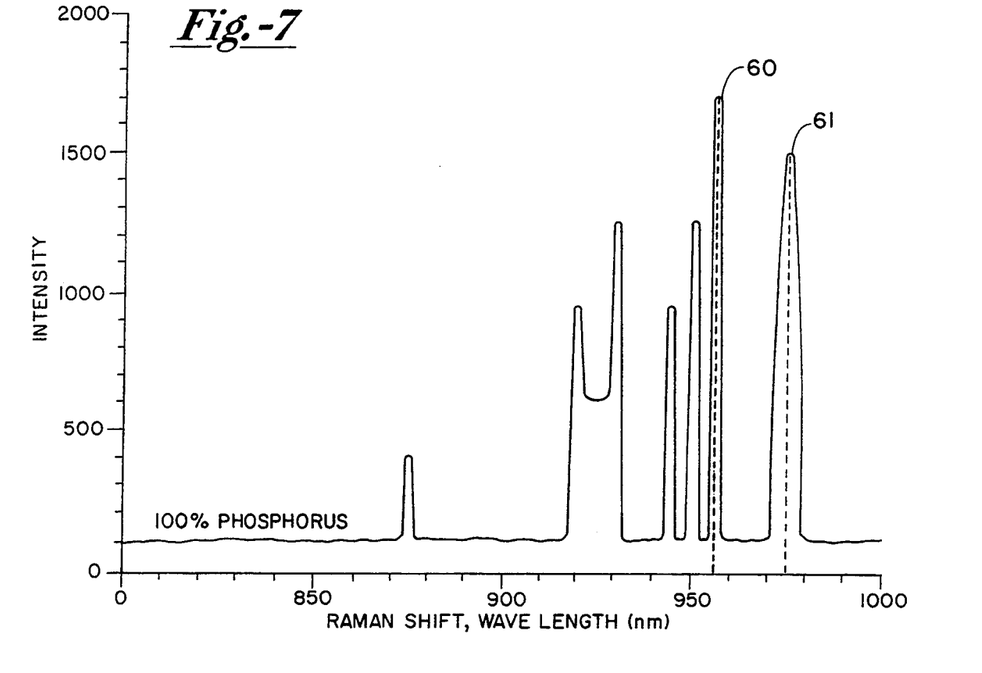
Figure 8:
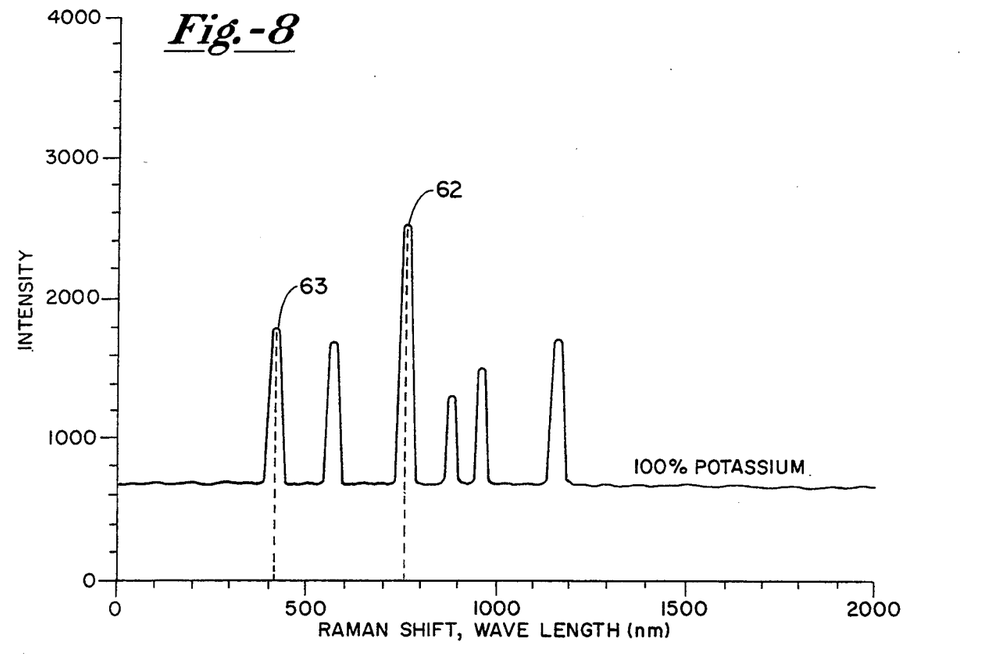

FIGS. 3, 4 and 5 represent three different spectral images obtained from the same soil scene when radiated by the source at the respective ideal wavelength mentioned, wherein the soil scene comprises 25% nitrogen, 20% phosphorous and 30% potassium. Referring to FIG. 6, a spectral image of a soil scene containing 100 percent nitrogen is shown. Similarly, a spectral image of a soil scene comprising 100% phosphorous and 100% potassium is shown in FIGS. 7 and 8, respectively. The operator stores in the memory of expert system 30 the intensity of the spectral peaks for soil scenes comprised of 100 percent of the respective chemical, as shown in FIGS. 6–8. In operation, expert system 30 compares the intensity of the peaks of the ascertained spectral images in FIGS. 3, 4 and 5 to intensity of the peaks stored in memory and shown in respective reference images shown in FIGS. 6, 7 and 8. For instance, the percentage of nitrogen in the soil scene is equal to the ratio of the peak intensity of FIG. 3 to the peak intensity image of FIG. 6 at common wavelengths, which intensities are stored in the memory of expert system 30. The ratio of phosphorous and potassium is calculated by expert system 30 in a similar manner using FIGS. 4–5 and 7–8.

This chemical composition measuring process is repeated for each of the elements of interest when system 10 is in operation, either sequentially using a single source at different frequencies, or in parallel using four sources having four different frequencies. The spectral image obtained, shown in FIG. 3, is compared against the spectral image of a soil scene consisting of 100 percent of the respective chemical of interest, such as shown in FIG. 6. Initially, expert system 30 first determines whether a certain element is present by comparing the obtained spectral image, such as FIG. 3, to the reference spectral image, such as FIG. 6 to ascertain if a spectral peak is present (exceeds a predetermined threshold) at the known florescence wavelength for the chemicals under study, such as at 50 for nitrogen, 52 for potassium, and 54 for phosphorous. If a spike is present, the amplitude of each of the ascertained peaks reference 50, 52, or 54, as shown in FIGS. 3, 4 and 5 is compared against the amplitude of the reference peaks 58, 60 and 62 of FIGS. 6, 7 and 8, representing a soil sample having 100 percent nitrogen, phosphorous and potassium, respectively. The combination of the spectral images shown in FIGS. 3, 4 and 5 is representative of the soil scene under study, and is commonly known as the soil signature.

To obtain an even more accurate calculation of the percentage of chemicals present at the soil scene, a separate peak different from 50, 52 and 54 peak frequency having the next higher intensity in FIGS. 3, 4 and 5, and identified at 51, 53 and 55, respectively, is compared to the intensity of the respective reference peak (at the same wavelength) also stored in memory and shown in FIGS. 6, 7 and 8, and identified at 59, 61 and 63. To obtain yet an even more accurate calculation of chemical content, the intensity of other peak frequencies shown in FIGS. 3–5 can be compared to the intensity of the corresponding reference peaks shown in FIGS. 6–8. By averaging or weighting the chemical content individually calculated using the different peak frequencies, errors due to measurement tolerances, or due to the possibility some elements will produce peaks at lower intensities at a same frequency when excited, can be reduced.

Spectrograph 28 also determines the soil type at the soil scene by ascertaining the water content of the soil scene, as moisture in the soil sensed in the furrow is indicative of the type of soil. For instance, soil comprised of clay will retain more moisture than sand or silt, and the ratios of the water holding capabilities for each of the soil types is known. Spectrograph 28 is used to produce a spectral radiance of water present at the soil scene. This spectrograph is then compared to a reference spectrograph stored in expert system 30 and indicative of a soil scene with a pre-determined percentage of water. The intensities of the spectrums at a peak frequency are compared by expert system 30 to ascertain the percentage of water in the soil. Once this percentage of moisture is known, expert system 30 characterizes the soil scene as a percentage of clay, silt or other well-known types of soil based on the relative moisture holding capabilities of each soil type by referencing a data table stored in the memory of expert system 30.

Once expert system 30 obtains the percentage of chemicals in the soil at the soil scene, as well as the type of soil present, expert system 30 then proceeds to utilize the chemical information received to create a chemical prescription or recommendation for the dispensing control system to follow. Control signals are then generated by expert system 30 as a function of vehicle speed to application system 22 via line 36, including the proper dispensing rate for the various chemicals from bins 14 by dispenser 20. For instance, if expert system 30 determines the soil scene to have 5 percent nitrogen, and the soil is comprised of clay, a chemical prescription of nitrogen is ascertained from a data table in expert system 30 memory. However, if expert system 30 determines, using the spectrograph 28, that the soil is comprised of sand, a different chemical prescription for nitrogen is established for application system 22 from expert system 30 data tables. Expert system 30 can take into account many other variables as well to determine the chemical prescriptions for each of the chemicals which are to be dispensed from bins 14 by dispenser 20. For instance, soil analyzer 28 can determine organic matter percentages at the soil scene, and how coarse the soil is which can be indicative of the fertilizer retaining properties of the soil. Thus, expert system 30 is well suited to utilize many variables in conjunction with the determined percentages of fertilizers present at the soil scene when creating the chemical prescription for controlling application system 22.

Other support systems are provided as well, such as a printer 40 for providing a printout of the system status, a keyboard system 42 for programming and entering data into expert system 30, and a monitor 44 for providing a visual status of the application system 10 to the operator. Expert system 30, printer 40, keyboard 42 and monitor 44 all reside within the cab of the vehicle. A variety of speed sensors 32 provide expert system 30 with the speed of the vehicle in real-time, which speed sensors are well-known in the art. The dispensing rate is determined as a function of the chemical prescriptions and vehicle speed.

While utilizing a spectrograph using spectroradiometry is the preferred soil analyzer used in the preferred embodiment of the present invention, it is recognized that the basic principles of spectroradiometry can be applied using microwave or ultrasonic techniques as well. For instance, stimulating the soil scene with a signal at a preselected fixed frequency with microwave or ultrasonic sources will induce returned signals comprised of multiple frequencies, known as the soil signature, and which soil signatures are indicative of the elements present in the soil scene. Thus, limitation to implementing a spectrograph is not to be inferred. Rather, the general principle of exciting soil at a predetermined fixed frequency, which chosen frequency is ideal to sense the presence and quantity of a particular element, to obtain a composite of signals returned from the soil scene is contemplated, and can be implemented in near real-time. For instance, exciting a soil scene with an illumination source at 1247 nm. will maximally excite the first order atoms of nitrogen due to quantum-mechanics. Different fixed frequencies can be generated for sensing different desired elements. Thus again, while a fixed frequency signal is used as a source, such as that produced by a laser in the visual range of the spectrum, other sources such as microwave signal generators and ultrasonic generators can be used as well, with varying sensing techniques.

OPERATION

Figure 9:
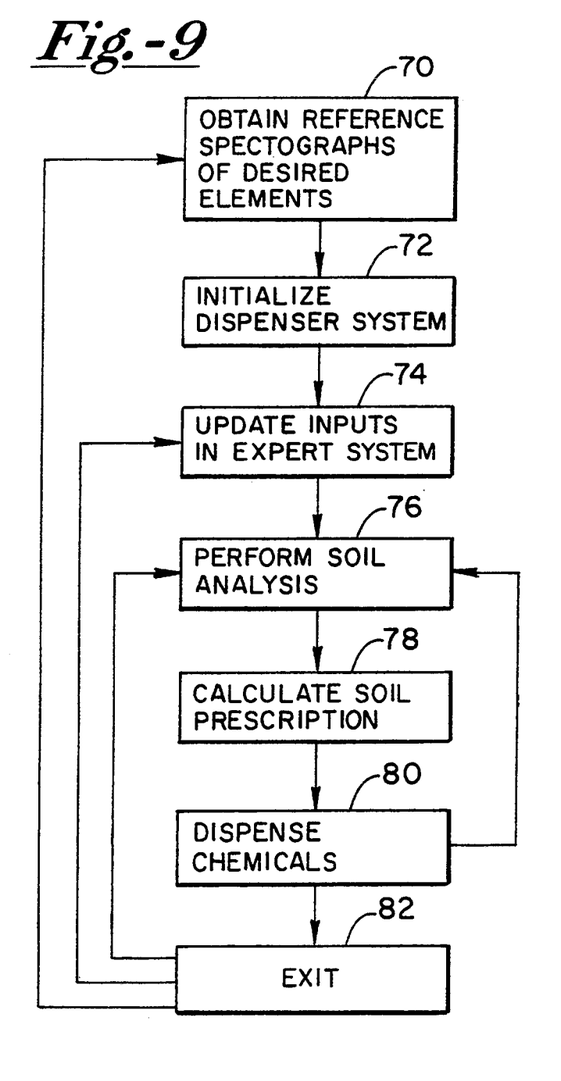
FIG. 9 is a flow diagram of the operation for the closed-loop application system.

Referring now to FIG. 9, a flow diagram for operation of the present closed-loop chemical application system 10 is illustrated. At step 70, the operator first obtains reference spectrographs for soil scenes which include 100 percent of the desired elements to be sensed, such as shown in FIGS. 5, 6, 7 and 8, and for a fixed percentage of water. For instance, the spectrograph of soil comprising of 100 percent nitrogen is obtained, and similarly, a spectrograph for each of the other elements including phosphorous, potassium and zinc is obtained from a soil scene comprising of 100 percent of the respective elements. The amplitudes of the peak frequencies at the appropriate wavelength obtained in each of the reference spectrographs are stored in memory in expert system 30.

Next, application system 22 is initialized at step 72. At this step, the bins are checked and loaded with appropriate chemicals to be dispensed such that the dispenser is ready to dispense the appropriate chemicals at a rate determined by expert system 30.

At step 74, the reference tables of expert system 30 are updated, wherein input from soil scientists can be updated. The inputs consist of various information, including tables for determining the type of soil based on water content, tables for determining the desired fertilizer levels for different types of fertilizers for each type of soil, and tables for determining dispensing rates of fertilizer based on the desired fertilizer level and the sensed fertilizer levels. Expert system 30 utilizes these tables to determine a chemical prescription.

Next, at step 76, soil analysis of the soil scene is performed in real-time by soil analyzer 28 as vehicle 12 traverses the field. Spectrographs of the soil scene are obtained by the soil analyzer 28 located behind the knife 26 in the furrow as the vehicle traverses the field. Spectrographs of each chemical of interest, and for water, are obtained. The spectrographs are communicated to expert system 30, wherein expert system 30 calculates the chemical prescriptions for the soil scene at step 78. This is done by first comparing the obtained spectrographs (FIGS. 3, 4 and 5) to the stored reference spectrographs (FIGS. 6, 7 and 8) determined in step 70. By comparing the spectrographs, the presence of the different chemicals are determined, wherein the percentage of the chemicals present is ascertained by determining the ratio of the intensities of the spectrograph at one or more peak frequencies (FIGS. 3, 4 and 5) to the intensities of the referenced spectrographs (FIGS. 6, 7 and 8) at the respective peak frequencies determined in step 70.

The type of soil present at the soil scene is also determined by the expert system 30 by comparing the obtained spectrograph for water to the reference spectrograph, and then tables stored in expert system 30 memory at step 74 are used to characterize the soil type based on the percentage of water present. Then, appropriate data tables of expert system 30 are referenced to determine the soil prescription. For instance, if the soil scene is determined to be clay based on water content, and 5 percent nitrogen is present, the table would indicate given these conditions a nitrogen level of 10 percent is desired. This would be the soil prescription. Expert system 30 then determines vehicle speed from sensor 32, and promptly sends the appropriate command signal to the dispenser 20 to establish the appropriate dispensing rate such that given the vehicle speed, a 10 percent nitrogen level is established at the soil scene. Thus, at step 80, dispenser 20 dispenses the appropriate chemicals of the appropriate rate. The dispensing of chemicals via dispenser 20 is timed to account for vehicle speed, respective time delays of the components, and the separation between analyzer 28 and dispenser 20 such that dispenser 20 dispenses the appropriate chemicals when it is over the soil scene analyzed by soil analyzer 28.

Steps 76 through 80 are continually repeated as vehicle 12 traverses the field. The application procedure can be terminated by the operator at any time by exciting the routine at step 82. The closed-loop system can be initiated again by returning to step 76, wherein the closed-loop procedure continues again such that the appropriate rate of chemicals is dispensed as the vehicle traverses the field. Alternatively, the routine can return to step 74 to update the input, such as data tables, in the expert system 30 by providing more input from the soil scientists. The routine can also be re-initialized by proceeding directly back to step 76 to store additional or different spectrographs used as the reference spectrographs.

The closed-loop routine is realized by continuously executing step 76, 78 and 80 to continuously perform soil analysis in near real-time, calculating the soil prescription in near real-time based on the results of the soil analysis, and then dispensing chemicals at the appropriate rate to the soil scene according to the soil prescription determined in step 78 using soil tables and the vehicle speed. In step 80, the dispensing rate is determined by taking account of the vehicle speed along with the chemical prescription such that the appropriate dispensing rate is determined and commanded in step 80. Step 80 also takes into account the distance between the soil sensor 28 and dispenser 20. Knowing the speed of the vehicle, the time elapsed between when soil analyzer 28 passes over a particular soil scene, and when dispenser 20 passes over the same scene, is taken into account such that the appropriate amount of chemicals is dispensed at the soil scene.

Step 76 consumes approximately 30 milliseconds, step 78 consumes approximately 100 milliseconds, and the time delay for the dispenser 20 to respond to the dispensing rate instruction at step 80 is approximately 0.5 seconds. Thus, for a vehicle traveling 18 mph, an overall processing time of 0.63 seconds is required. Thus, the minimum separation of soil analyzer 28 and dispenser 20 is 17 feet. By affixing support structure 24 to the frame of vehicle 12 to dispose soil sensor 28 forward of the dispenser 20 to establish a separation of say 20 feet, the dispensing system 10 will always have sufficient time to perform soil analysis, calculate the soil prescription and subsequently dispense the chemicals onto the soil scene. The faster vehicle 12 is traversing the field, obviously, the larger the required minimum spacing of soil analyzer 28 from dispenser 20. Any spacing of the soil sensor from dispenser 20 in excess of the minimum separation can be taken account by delaying the control signals from expert system 30 to dispenser 20 and this provides a time margin.

This invention has been described herein in considerable detail in order to comply with the Patent Statutes and to provide those skilled in the art with the information needed to apply the novel principles and to construct and use such specialized components as are required. However, it is to be understood that the invention can be carried out by specifically different equipment and devices, and that various modifications, both as to the equipment details and operating procedures, can be accomplished without departing from the scope of the invention itself.

I claim:

1. An apparatus for treating an area of soil, comprising:
   (a) a vehicle capable of traversing a field;
   (b) soil analysis means coupled to said vehicle for obtaining a soil signature indicative of a content of at least one element at a soil scene, comprising:
      (i) means for generating a first signal at a predetermined fixed frequency and directing said first signal upon the soil scene; and
      (ii) means for detecting a returned second signal from the soil scene induced by the first signal, said second signal composed of a plurality of frequencies and defining the soil signature; and
   (c) means coupled to the vehicle for dispensing a quantity of the element as a function of the soil signature.

2. The apparatus as specified in claim 1 wherein said soil analysis means further comprises means for determining soil type at said soil scene, wherein said dispensing means dispenses said element as a function of said soil type.

3. The apparatus as specified in claim 1 further comprising a means for sensing vehicle speed, wherein said dispensing means dispenses said element as a function of said vehicle speed.

4. The apparatus as specified in claim 1 wherein said detecting means performs real-time averaging of said detected second signals, and dispenses said element as a function of said averaged second signal.

5. The apparatus as specified in claim 1 wherein said detected soil signature is indicative of nitrogen, phosphorous, and potassium present at the soil scene.

6. The apparatus as specified in claim 1 wherein said soil analysis means comprises a spectrograph.

7. The apparatus as specified in claim 1 wherein said dispensing means is positioned a pre-determined distance behind said soil analysis means.

8. The apparatus as specified in claim 1 wherein said soil analysis means further comprises:
   (iii) means for determining an intensity of said returned second signal; and
   (iv) means for determining a percentage of the element in the soil from said second signal intensity.

9. The apparatus as specified in claim 8 further comprising means coupled to said vehicle for preparing said soil scene.

10. The apparatus as specified in claim 8 wherein said percentage determining means comprises:
    (a) means for storing a pre-determined value indicative of a known percentage of said element; and
    (b) means for comparing said pre-determined value to the determined intensity of the second signal to obtain an output, said output indicative of the percentage of the element in the soil scene.

11. The apparatus as specified in claim 1 wherein said soil analysis means implements ultrasonic waves.

12. The apparatus as specified in claim 1 wherein said soil analysis means implements microwaves.

13. An apparatus for treating an area of soil, comprising:
   (a) a vehicle capable of traversing a field;
   (b) soil analysis means coupled to said vehicle for obtaining a soil signature indicative of a content of at least one element present at a soil scene, comprising:
      (i) means for generating a first signal at a predetermined fixed frequency and directing said first signal upon the soil scene; and
      (ii) means for sensing a returned second signal induced by said first signal and having a frequency different form the frequency of the first signal and defining the soil signature; and
   (c) means coupled to the vehicle for dispensing a quantity of the element as a function of the soil signature.

14. The apparatus as specified in claim 13 wherein said soil analysis means comprises:
   (iii) means for determining an intensity of said returned second signal; and
   (iv) means for determining a percentage of the element in said soil scene from said second signal intensity.

15. The apparatus as specified in claim 14 wherein said percentage determining means comprises:
   (a) means for storing a pre-determined value indicative of a known percentage of said element; and
   (b) means for comparing said pre-determined value to the determined intensity of the second signal to obtain an output, said output indicative of the percentage of the element in the soil scene.

16. A method of treating agricultural land comprising the steps of:
   (a) ascertaining a current element level of a soil scene by:
      (i) exciting the soil scene with a signal of a predetermined fixed frequency;
      (ii) sensing a second signal induced by said first signal from said soil scene, said second signal comprising a plurality of frequencies; and
      (iii) comparing said second signal to a reference signal to determine the element level of said soil scene;
   (b) determining a soil prescription based on said soil type and said second signal; and
   (c) applying the element to said soil scene as a function of said determined soil prescription.

17. The method of claim 16 wherein said method is performed in near real-time.

18. The method of claim 16 further comprising the step of:
   (d) ascertaining a speed of a vehicle adapted to apply the element to the soil scene in step (c) and applying the element to the soil scene in step (c) as a function of said vehicle speed.

19. The method of claim 16 further comprising the step of:
   (d) ascertaining a soil type of the soil scene and applying the element to the soil scene in step (c) as a function of said soil type.

20. The method of claim 16 further comprising the step of providing a RAMAN spectrograph to execute the step (a).

* * * * *

UNITED STATES PATENT AND TRADEMARK OFFICE
CERTIFICATE OF CORRECTION

PATENT NO. : 5,355,815
DATED : October 18, 1994
INVENTOR(S) : Robert J. Monson

It is certified that error appears in the above-indentified patent and that said Letters Patent is hereby corrected as shown below:

Column 10, line 55, after "soil" insert -- scene --.

Column 11, line 15, "form" should read -- from --.

Signed and Sealed this

Sixth Day of December, 1994

Attest:

BRUCE LEHMAN

*Attesting Officer*     *Commissioner of Patents and Trademarks*